(12) United States Patent
Niederberger et al.

(10) Patent No.: US 10,898,210 B2
(45) Date of Patent: Jan. 26, 2021

(54) SEPARABLE GUIDE INSTRUMENT FOR ANATOMICAL IMPLANT

(71) Applicant: DePuy Synthes Products, Inc., Raynham, MA (US)

(72) Inventors: Alfred Niederberger, Grenchen (CH); Johann Fierlbeck, Salzburg (AT)

(73) Assignee: DePuy Synthes Products, Inc., Raynham, MA (US)

( * ) Notice: Subject to any disclaimer, the term of this patent is extended or adjusted under 35 U.S.C. 154(b) by 258 days.

(21) Appl. No.: 16/190,815

(22) Filed: Nov. 14, 2018

(65) Prior Publication Data
US 2019/0076157 A1 Mar. 14, 2019

Related U.S. Application Data

(62) Division of application No. 14/633,487, filed on Feb. 27, 2015, now Pat. No. 10,159,503.
(Continued)

(51) Int. Cl.
| | |
|---|---|
| *A61B 17/88* | (2006.01) |
| *A61B 17/17* | (2006.01) |
| *A61B 17/80* | (2006.01) |

(52) U.S. Cl.
CPC ...... *A61B 17/1728* (2013.01); *A61B 17/8057* (2013.01); *A61B 17/1735* (2013.01); *A61B 17/808* (2013.01)

(58) Field of Classification Search
CPC combination set(s) only.
See application file for complete search history.

(56) References Cited

U.S. PATENT DOCUMENTS

| | | | |
|---|---|---|---|
| 6,245,082 B1 | 6/2001 | Gellman et al. | |
| 6,767,355 B2 | 7/2004 | Frova et al. | |

(Continued)

FOREIGN PATENT DOCUMENTS

| | | |
|---|---|---|
| CN | 1909845 A | 2/2007 |
| CN | 101374471 A | 2/2009 |

(Continued)

OTHER PUBLICATIONS

"Philos and Philos Long, The anatomic fixation system for the proximal humerous." Technique Guide, Synthes, Jun. 2010, 30 pages.
(Continued)

*Primary Examiner* — Sameh R Boles
(74) *Attorney, Agent, or Firm* — BakerHostetler (57) ABSTRACT

A separable surgical guide instrument is configured to be inserted minimally invasively into a patient's soft tissue, and includes a guide body and a guide aperture that extends through the guide body. The guide body has a distal end that includes a first distal end portion and a second distal end portion that are arranged such that at least one of the first and second distal end portions is movable with respect to the other of the first and second distal end portions between 1) a closed position whereby the first and second distal end portions are concurrently insertable into a bone fixation aperture of a bone plate, and 2) an open position whereby the first distal end portion is spaced from the second distal end portion a sufficient distance such that the first and second distal end portions are not concurrently insertable into the bone fixation aperture.

14 Claims, 6 Drawing Sheets

Related U.S. Application Data

(60) Provisional application No. 61/949,524, filed on Mar. 7, 2014.

(56) References Cited

U.S. PATENT DOCUMENTS

| | | |
|---|---|---|
| 6,849,064 B2 | 2/2005 | Hamada |
| 2002/0077655 A1 | 6/2002 | Frova |
| 2005/0038444 A1 | 2/2005 | Binder et al. |
| 2005/0234467 A1 | 10/2005 | Rains |
| 2006/0089651 A1 | 4/2006 | Trudeau et al. |
| 2006/0106399 A1 | 5/2006 | Taras et al. |
| 2008/0015591 A1 | 1/2008 | Castaneda et al. |
| 2008/0132904 A1 | 6/2008 | Usher et al. |
| 2009/0076556 A1 | 3/2009 | McGarity et al. |
| 2009/0281543 A1 | 11/2009 | Orbay et al. |
| 2010/0057138 A1 | 3/2010 | Muerner et al. |
| 2014/0243837 A1 | 8/2014 | Mebarak |
| 2015/0119943 A1* | 4/2015 | Milella, Jr. ........ A61B 17/8057 606/281 |

FOREIGN PATENT DOCUMENTS

| | | |
|---|---|---|
| CN | 103200887 A | 7/2013 |
| EP | 2158863 A1 | 3/2010 |
| JP | 2010-057904 A | 3/2010 |
| WO | 20111154891 A2 | 12/2011 |

OTHER PUBLICATIONS

"Peri-Loc Locked plating system, Locking Small Fragment Overiew," Surgical Technique, Smith & Nephew, Oct. 2010, 68 pages.

\* cited by examiner

SEPARABLE GUIDE INSTRUMENT FOR ANATOMICAL IMPLANT

CROSS-REFERENCE TO RELATED APPLICATIONS

This is a divisional of Ser. No. 14/633,487 filed Feb. 27, 2015, which in turn claims the benefit of U.S. Patent Application No. 61/949,524 filed Mar. 7, 2014, the disclosure of each of which is hereby incorporated by reference as if set forth in its entirety herein.

BACKGROUND

During orthopedic surgical procedures, a surgeon will often insert a plurality of bone anchors through a respective bone fixation apertures of a bone plate and into an underlying bone so as to attach the bone plate to the underlying bone. Certain bone plates can define internally threaded bone fixation apertures, and the bone anchors can define externally threaded heads that are configured to threadedly mate with the bone plate in the bone fixation aperture. Thus, it can be desirable to ensure that the bone anchor is aligned with the bone fixation aperture.

SUMMARY

In accordance with one embodiment, a separable surgical guide instrument includes a guide body that defines a proximal end and a distal end spaced from the proximal end. The separable surgical guide instrument further defines a guide aperture that extends through the guide body from the proximal end to the distal end. The distal end can include a first distal end portion and a second distal end portion that are arranged such that at least one of the first and second distal end portions is movable with respect to the other of the first and second distal end portions between 1) a closed position whereby the first and second distal end portions are concurrently insertable into a bone fixation aperture of a bone plate, and 2) an open position whereby the first distal end portion is spaced from the second distal end portion a sufficient distance such that the first and second distal end portions are not concurrently insertable into the bone fixation aperture.

BRIEF DESCRIPTION OF THE DRAWINGS

The foregoing summary, as well as the following detailed description of illustrative embodiments of the instrument of the present disclosure, will be better understood when read in conjunction with the appended drawings. It should be understood, however, that the application is not limited to the precise schematics and arrangements shown. In the drawings.

DETAILED DESCRIPTION

Referring to FIGS. 1A-2A, a bone fixation assembly 20 can include a separable surgical guide instrument 22, a bone plate 24, and at least one bone anchor 26 such as a plurality of bone anchors 26. The bone plate 24 includes a bone plate body 28 defining an inner surface 28a configured to face an underlying bone 25, and an outer surface 28b opposite the inner surface 28a. The bone plate 24 can further include a plurality of bone fixation apertures 30 that extend through the bone plate body 28 from the outer surface 28b to the inner surface 28a. Each of the bone fixation apertures 30 can be defined by an interior surface 32. At least one of the bone fixation apertures 30 can be threaded. Accordingly, at least a portion the interior surface 32 of at least one of the bone fixation apertures 30 can be threaded. For instance, a plurality of the bone fixation apertures 30, up to and including all of the bone fixation apertures 30 can be threaded. At least one up to all of the bone anchors 26 can include an anchor head 26a and a shaft 26b that extends from the head. The shaft 26b can be threaded so as to threadedly purchase with the underlying bone 25. The head 26a can be threaded so as to threadedly mate with the bone plate 24 in a respective one of the bone fixation apertures 30.

Figure 1A:
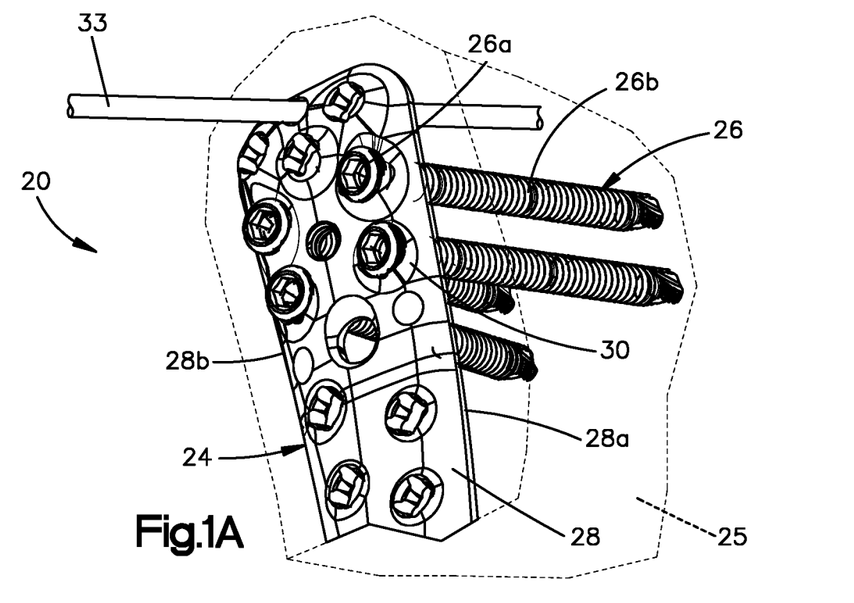
FIG. 1A is a perspective view of a bone plate affixed to an underlying bone in accordance with one embodiment.
Figure 1B:
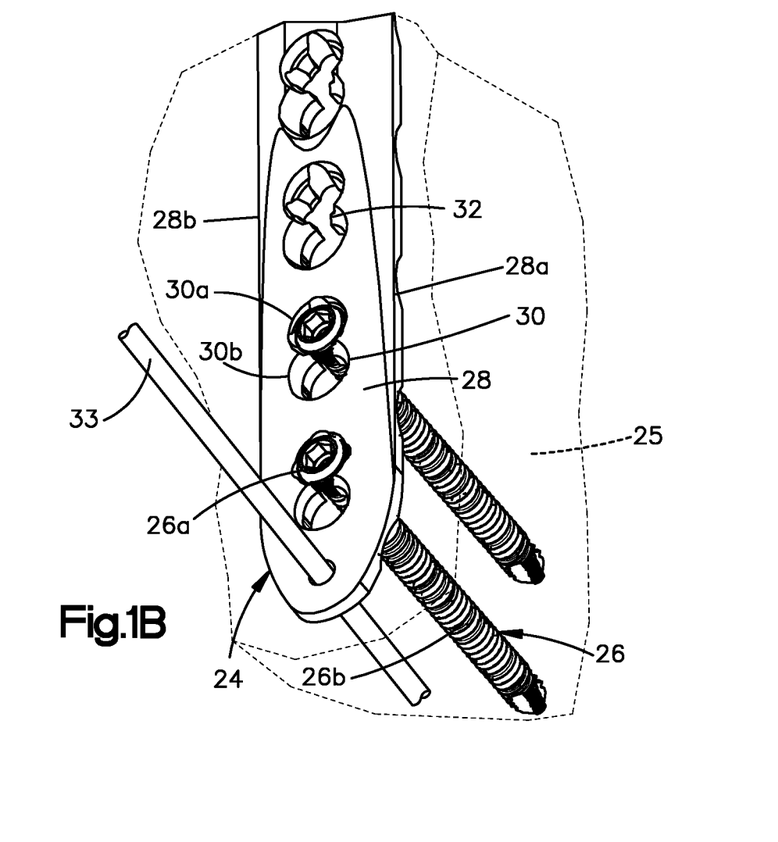
FIG. 1B is a perspective view of a bone plate affixed to an underlying bone in accordance with another embodiment.

As illustrated in FIG. 1A, the interior surface 32 can define an enclosed circumference of the threaded bone fixation aperture 30, and an entirety of the circumference of the interior surface 32 can be threaded along at least a portion of its length from the outer surface 28b to the inner surface 28a. For instance, the interior surface 32 can be threaded along an entirety of its length from the outer surface 28b to the inner surface 28a. At least a portion up to an entirety of the interior surface 32 can further be conical or alternatively shaped as desired. It should be appreciated that at least one of the bone fixation apertures 30 can be unthreaded. Accordingly, the interior surface 32 that defines the at least one unthreaded bone fixation apertures 30 can be devoid of threads along an entirety of its length from the outer surface 28b to the inner surface 28a. For instance, a plurality of the bone fixation apertures 30 can be unthreaded. As illustrated in FIG. 1B, at least one of the bone fixation apertures 30 can be a combination aperture having a threaded portion 30a and at least one unthreaded portion 30b spaced from the threaded portion 30a along a length of the bone plate 24, and open to the threaded portion 30a. Thus, the at least partially threaded interior surface 32 can partially define the threaded portion 30a, which can also be referred to as a threaded bone fixation aperture. Accordingly, the threaded bone fixation aperture 30 can be at least partially defined by the threaded interior surface 32. For example, the threaded bone fixation aperture 30 can be defined by the interior surface 32 as illustrated in FIG. 1A, or partially defined by the interior surface 32 as illustrated in FIG. 1B. The unthreaded portion 30b is configured to receive a bone anchor having a head that is configured to compress the bone plate 24 against the underlying bone 25 when the head is seated in the unthreaded portion.

The bone fixation assembly 20 can further include at least one temporary fixation member 33 that is configured to secure the bone plate 24 to the underlying bone 25 prior to securing the bone anchors 26 to the bone plate 24 and the underlying bone 25. In accordance with one embodiment, the bone plate 24 can include at least one temporary fixation aperture 34 extends through the plate body 28 from the outer surface 28b to the inner surface 28a. The temporary fixation aperture 34 can have a diameter less than that of the bone fixation apertures 30. In one example, the temporary fixation member 33 can be configured as at least one Kirschner wire (K-wire) that is sized to be inserted through the temporary fixation aperture 34 and into the underlying bone 25 so as to temporarily secure the bone plate 24 to the underlying bone 25. While the temporary fixation member 33 can be configured as a K-wire as described above, it should be appreciated that the temporary fixation member 33 can be constructed in accordance with any suitable alternative embodiment. For instance, the temporary fixation member 33 can be configured as a clamp that is configured to temporarily secure the bone plate 24 to the underlying bone 25. After the temporary fixation member 33 has temporarily fixed the bone plate 24 to the underlying bone 25 in a desired position, the bone anchors 26 can be driven through the bone fixation apertures 30 and into the underlying bone 25 so as to secure the bone plate to the underlying bone 25. The temporary fixation member 33 can then be removed from the bone 25 and the bone plate 24. For instance, when the temporary fixation member 33 is configured as at least one K-wire, the at least one K-wire can be removed from the bone 25 and the bone plate 24. When the temporary fixation member is configured as at least one clamp, the clamp can be removed from the bone plate 24 and the bone 25 after the bone anchors 26 are secured in the bone 25. It should be appreciated that the temporary fixation member 33 can be suitably configured in accordance with any alternative embodiment that is capable of temporarily securing the bone plate 24 to the bone 25 until the bone anchors 26 have been secured.

Referring also to FIGS. 2A-2D, the separable surgical guide instrument 22 includes a guide body 36 and a guide aperture 38 that extends through the guide body 36. For instance, the guide aperture 38 can extend through the guide body 36 along a longitudinal direction 44. The guide aperture 38 can extend along a central axis C through the guide body 36. Thus, the central axis C can be oriented along the longitudinal direction 44. The guide body 36 is configured to move between a closed position and an open position. When the guide body 36 is in the closed position, the guide body is sized to be inserted into one of the bone fixation apertures 30 so as to couple the guide body 36 to the bone plate 24. In one example, a portion of the guide body 36 can be threaded so as to threadedly purchase with the bone plate 24 inside a threaded bone fixation aperture 30 when the guide body is in the closed position. Thus, when the guide body 36 is in the closed position, the guide aperture 38 is configured to guide a bone anchor 26 through the bone fixation aperture 30 and into the underlying bone 25. The guide body 36 can then be decoupled from the bone plate 24, and the bone anchor 26 can be further driven into the underlying bone 25 until the bone anchor head 26a is seated against the bone plate 24 in the bone fixation aperture 30. In accordance with one embodiment, prior to insertion of the bone anchor 26 into the guide aperture 38, the guide aperture 38 can guide a surgical drill through the bone fixation aperture 30 and into the underlying bone 25 so as to create a pilot opening in the underlying bone 25. Once the surgical drill is removed from the guide aperture 38, the bone anchor 26 can subsequently be driven into the pilot opening as it is fixed to the underlying bone 25.

It should be appreciated that when the separable surgical guide instrument 22 is in the closed position, the guide body 36 interferes with the bone anchor head 26a and prevents the bone anchor head 26a from being driven through the guide aperture 38 and out the guide body 36. When the separable surgical guide instrument 22 moves to the open position, the guide body 36 expands along a second direction 45 that is perpendicular to the longitudinal direction 44 so as to remove the interference with the bone anchor head 26a, thereby permitting the bone anchor head 26a to be driven through the guide aperture 38 and out the guide body 36. Accordingly, the bone anchor head 26a can be seated in the bone fixation aperture 30.

The guide body 36 defines a proximal end 40, a distal end 42 that is spaced from the proximal end 40 along the longitudinal direction 44. The guide aperture 38 can extend through the guide body 36 along the longitudinal direction 44 from the proximal end 40 to the distal end 42. The distal end 42 includes a first distal end portion 42a and a second distal end portion 42b that are arranged such that at least one of the first and second distal end portions 42a and 42b is movable with respect to the other of the first and second distal end portions 42a and 42b between a closed position and an open position. For instance, each of the first and second distal end portions 42a and 42b can be movable with respect to the other of the first and second distal end portions 42a and 42b between the closed position and the open position. When the first and second distal end portions 42a and 42b are in the closed position, the guide body 36 is in the closed position. When the first and second distal end portions 42a and 42b are in the open position, the guide body 36 is in the open position.

As described above, when the separable surgical guide instrument 22 is in the closed position, the guide body 36 interferes with the bone anchor head 26a and prevents the bone anchor head 26a from being driven through the guide aperture 38 and out the guide body 36. For instance, the distal end 42 can interfere with the bone anchor head 26a and prevent the bone anchor head 26a from being driven through the guide aperture and out the distal end 42 when the separable surgical guide instrument 22 is in the closed position. When the separable surgical guide instrument 22 moves to the open position, the guide body 36 expands along the second direction 45 so as to remove the interference between the distal end 42 and the bone anchor head 26a, thereby permitting the bone anchor head 26a to be driven through the guide aperture 38 and out the distal end 42. Accordingly, the bone anchor head 26a can be driven through the guide aperture 38 and can subsequently be seated in the bone fixation aperture 30.

For example, when the first and second distal end portions 42a and 42b are in the closed position, the first and second distal end portions 42a and 42b are concurrently insertable into the bone fixation aperture 30. When the first and second distal end portions 42a and 42b are in the open position, the first distal end portion 42a is spaced from the second distal end portion 42b a sufficient distance such that the first and second distal end portions 42a and 42b are not concurrently insertable into the bone fixation aperture 30. For instance, the distal end 42 is sized greater than the bone fixation aperture 30 when the first and second end portions 42a and 42b are in the open position. Accordingly, when the first and second distal end portions 42a and 42b are in the open position, the bone anchor head 26a, which can be threaded, is drivable through the guide aperture 38 along the longitudinal direction 44 from the proximal end 40 to the distal end 42, and out the distal end 42 such that the threaded bone anchor head 26a threadedly purchases with the bone plate 24 in the bone fixation aperture 30.

It should be further appreciated that the guide body 36 can define an inner surface 46 that at least partially defines the guide aperture 38, and an outer surface 48 opposite the inner surface 46. For instance, the outer surface 48 can be opposite the inner surface along the second direction 45. It should be appreciated that the inner surface 46 can be continuous from the proximal end 40 to the distal end 42. Alternatively, the inner surface 46 can be segmented. It should thus be appreciated that when the when the first and second distal end portions 42a and 42b are in the closed position, the inner surface 46 defines a first cross-sectional dimension at a select location S of the distal end 42. When the first and second distal end portions 42a and 42b are in the open position, the inner surface 46 defines a second cross-sectional dimension D2 at the select location S of the distal end 42 that is greater than the first cross-sectional dimension. Further, when the first and second distal end portions 42a and 42b are in the closed position, the inner surface 46 can substantially enclose the guide aperture 38 at the distal end 42. For instance, the inner surface 46 can substantially enclose the guide aperture 38 at the distal end 42 along a plane that is orthogonal to the longitudinal direction 44. When the first and second distal end portions 42a and 42b are in the closed position, the distal end 42 can define a gap that is disposed between the first and second distal end portions 42a and 42b, and extends from the outer surface 48 to the inner surface 46. Thus, the gap can be open to the guide aperture 38. Alternatively or additionally, the first and second distal end portions 42a and 42b can overlap each other or fully abut each other when in the closed position, such that the first and second distal end portions 42a and 42b continue to enclose the guide aperture 38 when in the open position.

With continuing reference to FIGS. 2A-2D, the first distal end portion 42a defines at least one first thread segment 50 at the outer surface 48, and the second distal end portion 42b defines at least one second thread segment 52 at the outer surface 48. When the first and second distal end portions 42a and 42b are in the closed, position, the first thread segment 50 is aligned with the second thread segment 52 along a common helix 54. Accordingly, when the first and second distal end portions 42a and 42b are in the closed position, the distal end 42 is configured to threadedly purchase with the bone plate 24 in the bone fixation aperture. The first and second thread segments 50 and 52 can be circumferentially continuous or segmented as desired. For instance, the at least one first thread segment 50 can include a plurality of first thread segment portions 56 spaced from each other along the longitudinal direction L. Similarly, the at least one second thread segment 52 can include a plurality of second thread segment portions 58 spaced from each other along the longitudinal direction L. When the first and second distal end portions 42a and 42b are in the closed, position, each of the first thread segment portions 56 align with respective ones of the second thread segment portions 58 along at least one common helix 54. Similarly, when the first and second distal end portions 42a and 42b are in the closed, position, each of the second thread segment portions 58 align with respective ones of the first thread segment portions 56 along at least one common helix 54.

The first and second distal end portions 42a and 42b can abut each other in the closed position, such that the first and second thread segments 50 and 52, and thus the first and second thread segment portions 56 and 58, are continuous with each other. When the first and second distal end portions are in the open position, the at least one first thread segment 50 is out of alignment with the at least one second thread segment 52. For instance, at least one up to all of the first thread segment portions 56 is out of alignment with all of the second thread segment portions 58. Similarly, at least one up to all of the second thread segment portions 58 is out of alignment with all of the first thread segment portions 56. It should be appreciated that thread segments, or thread segment portions, that are out of alignment do not extend along a common helix.

With continuing reference to FIGS. 2A-2D, the first distal end portion 42a and the second distal end portion 42b are pivotally supported with respect to each other about a pivot axis P. The pivot axis P can extend perpendicular to the longitudinal direction 44. Further, the pivot axis P can intersect a central axis of the guide aperture 38. The pivot axis P can be disposed at the proximal end 40 of the guide body 36. It should be appreciated, of course, that the pivot axis P can be disposed at any suitable location as desired. Accordingly, at least one of the first distal end portion 42a and the second distal end portion 42b is pivotable with respect to the other of the first distal end portion 42a and the second distal end portion 42b about the pivot axis P. In accordance with one embodiment, each of the first distal end portion 42a and the second distal end portion 42b is pivotable with respect to the other of the first distal end portion 42a and the second distal end portion 42b.

In one example, the guide body 36 includes a first guide member 60 and a second guide member 62. The first guide member 60 can define the first distal end portion 42a, and the second guide member 62 can define the second distal end portion 42b. Thus, the first and second guide members 60 and 62 are movable between the open position and the closed position, which causes the first and second distal end portions 42a and 42b to move between the open position and the closed position. It should thus be appreciated that reference to one or more of the first and second distal end portions 42a and 42b in the open position or closed position, the first and second guide members 60 and 62 in the open position or closed position, and the guide body 36 in the open position or closed position can apply equally to all others of the second distal end portions 42a and 42b in the open position or closed position, the first and second guide members 60 and 62 in the open position or closed position, and the guide body 36 in the open position or closed position, respectively, unless otherwise indicated. The first guide member 60 can define a first proximal end portion 72 opposite the first distal end portion 42a. The second guide member 62 can define a second proximal end portion 74 opposite the second distal end portion 42b. The first guide member 60 defines a first outer surface 64 and a first inner surface 66 opposite the first outer surface 64. Similarly, the second guide member 62 defines a second outer surface 68 and a second inner surface 70 opposite the second outer surface 68.

The first and second inner surfaces 66 and 70 can combine to define the inner surface 46 of the guide body 36. The first and second outer surface 64 and 68 can combine to define the outer surface 48 of the guide body 36. The first inner surface 66 faces the guide aperture 38 when the first and second guide members 60 and 62 are in the closed position. Similarly, the second inner surface 70 faces the guide aperture 38 when the first and second guide members 60 and 62 are in the closed position. For instance, when the first and second guide members 60 and 62 are in the closed position, the first and second inner surfaces 66 and 70 can cooperate so as to at least partially define the guide aperture 38. Thus, it can be said that the first inner surface 66 can at least partially define the guide aperture 38. It can similarly be said that the second inner surface 70 at least partially defines the guide aperture 38.

The select location S of the distal end 42 can have an outer dimension from the first outer surface 64 to the second outer surface 68 through the central axis C axis of the guide aperture 38 when the first and second distal end portions 42a and 42b are in the closed position. The select location S further has an inner dimension from the first inner 66 surface to the second inner surface 70 through the central axis C when the first and second distal end portions 42a and 42b are in the open position. In accordance with one embodiment, the inner dimension is at least equal to the outer dimension. For instance, in one example, the inner dimension is at least equal to the outer dimension. The select location S can be positioned so as to be inserted in the bone fixation aperture 30 during operation. Accordingly, the outer surface at the select location S can threadedly mate with the bone plate 24 in the bone fixation aperture 30. The inner and outer dimensions and can be measured along a direction perpendicular to the longitudinal direction 44 and central axis C.

The distal end 42 can be tapered toward the central axis C along a direction from the proximal end 40 toward the distal end 42. For instance, at least a portion of the distal end 42 can be conically tapered toward the central axis C along the direction from the proximal end 40 toward the distal end 42. In one example, an entirety of the distal end 42 can be conically tapered toward the central axis C along the direction from the proximal end 40 toward the distal end 42. For example, the first outer surface 64 at the first distal end portion 42a defines a first tapered surface 76 that is tapered toward the central axis C along a direction from the first proximal end portion 72 toward the first distal end portion 42a. Similarly, the second outer surface 68 at the second distal end portion 42b a second tapered surface 78 that is tapered toward the central axis C along a direction from the second proximal end portion 74 toward the second distal end portion 42b. The at least one first thread segment 50 can be defined by the first distal end portion 42a at the first outer surface 64. For instance, the at least one first thread segment 50 can be disposed along at least a portion of the first tapered surface 76. The first thread segment portions 56 can be disposed along at least a portion of the first tapered surface 76. In one example, the at least one first thread segment 50 can be disposed along an entirety of the first tapered surface 76. Thus, the first thread segment portions 56 can be disposed along an entirety of the first tapered surface 76. The at least one second thread segment 52 can be defined by the second distal end portion 42b at the second outer surface 68. For instance, the at least one second thread segment 52 can be disposed along at least a portion of the second tapered surface 78. The second thread segment portions 58 can be disposed along at least a portion of the second tapered surface 78. In one example, the at least one second thread segment 52 can be disposed along an entirety of the second tapered surface 78. Thus, the second thread segment portions 58 can be disposed along an entirety of the second tapered surface 78.

With continuing reference to FIGS. 2A-2D, the first guide member 60 defines a first face 80 that extends between the first inner surface 66 and the first outer surface 64. The first guide member 60 can further define a first recess 82 that extends into the first face 80 and divides the first face 80 into a first segment 80a of the first face 80, and a second segment 80b of the first face 80. For instance, the first recess 82 can extend into the first face 80 along a direction from the first inner surface 66 toward the first outer surface 64. The first recess 82 can define an outer perimeter defined by the first inner surface 66. In one example, at least a portion of the outer perimeter of the first recess 82 can be arc-shaped along a plane that extends normal to at least one or both of the first inner surface 66 and the first outer surface 64. The plane can be normal to the central axis C when the guide body 36 is in the closed position. It should be appreciated, of course, that the first recess 82 can define any size and shape as desired.

Similarly, the second guide member 62 defines a second face 84 that extends between the second inner surface 70 and the second outer surface 68. The second guide member 62 can further define a second recess 86 that extends into the second face 84 and divides the second face 84 into a first segment 84a of the second face 84, and a second segment 84b of the second face 84. For instance, the second recess 86 can extend into the second face 84 along a direction from the second inner surface 70 toward the second outer surface 68. The second recess 86 can define an outer perimeter defined by the second inner surface 70. In one example, at least a portion of the outer perimeter of the second recess 86 can be arc-shaped along a plane that extends normal to at least one or both of the second inner surface 70 and the second outer surface 68. The plane can be normal to the central axis C when the guide body 36 is in the closed position. It should be appreciated, of course, that the second recess 86 can define any size and shape as desired.

The first recess 82 can define a first portion of the guide aperture 38. The second recess 86 can define a second portion of the guide aperture 38 that is different than the first portion. In one example, the first and second portions can define equal halves of the guide aperture 38. The first and second recesses 82 and 86 can combine to at least partially define the guide aperture 38 when the first and second guide members 60 and 62 are in the closed position. The first and second faces 80 and 84 can face each other when the first and second guide members 60 and 62 are in the closed position. In one example, the first and second faces 80 and 84 can abut each other when the first and second guide members 60 and 62 are in the closed position. The first and second faces 80 and 84 can be spaced from each other so as to define a gap therebetween when the first and second guide members 60 and 62 are in the open position. Similarly, the first and second inner surfaces 66 and 70 can abut each other when the guide body 36 is in the closed position. The first and second inner surfaces 66 and 70 can be spaced from each other when the guide body 36 is in the open position. Similarly, the first and second outer surfaces 64 and 68 can abut each other when the guide body 36 is in the closed position. The first and second outer surfaces 64 and 68 can be spaced from each other when the guide body 36 is in the open position. It should be appreciated, of course, that the first and second guide members 60 and 62, and the first and second distal end portions 42a and 42b can be constructed in accordance with any suitable alternative as desired. For instance, the first and second distal end portions 42a and 42b can overlap each other, both when in the closed position, and when in the open position.

The first and second guide members 60 and 62 can include respective first and second alignment members that are configured to engage each other so as to attach the first and second guide members 60 and 62 to each other when the first and second guide members 60 and 62 are in the closed position. The first and second alignment members are configured to disengage each other so as to detach the first and second guide members 60 and 62 from each other when the first and second guide members 60 and 62 move from the closed position to the open position. At least one of the first and second guide members 60 and 62 defines a projection 102 that extends from the respective one of the first and second faces 80 and 84, and the other of the first and second guide members 60 and 62 defines an opening 104 that extends into the respective other of the first and second faces 80 and 84. The opening 104 is configured to receive the projection 102 when the first and second guide members 60 and 62 are in the closed position. In one example, the first guide member 60 defines a first projection 102a and a first opening 104a disposed adjacent the first projection 102a. The second guide member 62 can define a second projection 102b and a second opening 104b disposed adjacent the second projection 102b. The first projection 102a and the second opening 104b can be operably aligned with each other such that the first projection 102a is inserted into the second opening 104b when the first and second guide members 60 and 62 are in the closed position. Similarly, the first opening 104a and the second projection 102b can be operably aligned with each other such that the second projection 102b is inserted into the first opening 104a when the first and second guide members 60 and 62 are in the closed position. Thus, the first and second thread segments 50 and 52 can be aligned with each other along the common helix 54 when the first and second guide members 60 and 62 are in the closed position.

The first projection 102a can extend out from the first segment 80a of the first face 80, and the first opening 104a can extend into the second segment 80b of the first face 80. The second opening 104b can extend into the first segment 84a of the second face 84. The second projection can extend out from the second segment 84b of the second face 84. It should be appreciated that the first and second alignment members can be alternatively configured and positioned as desired.

Figure 2A:
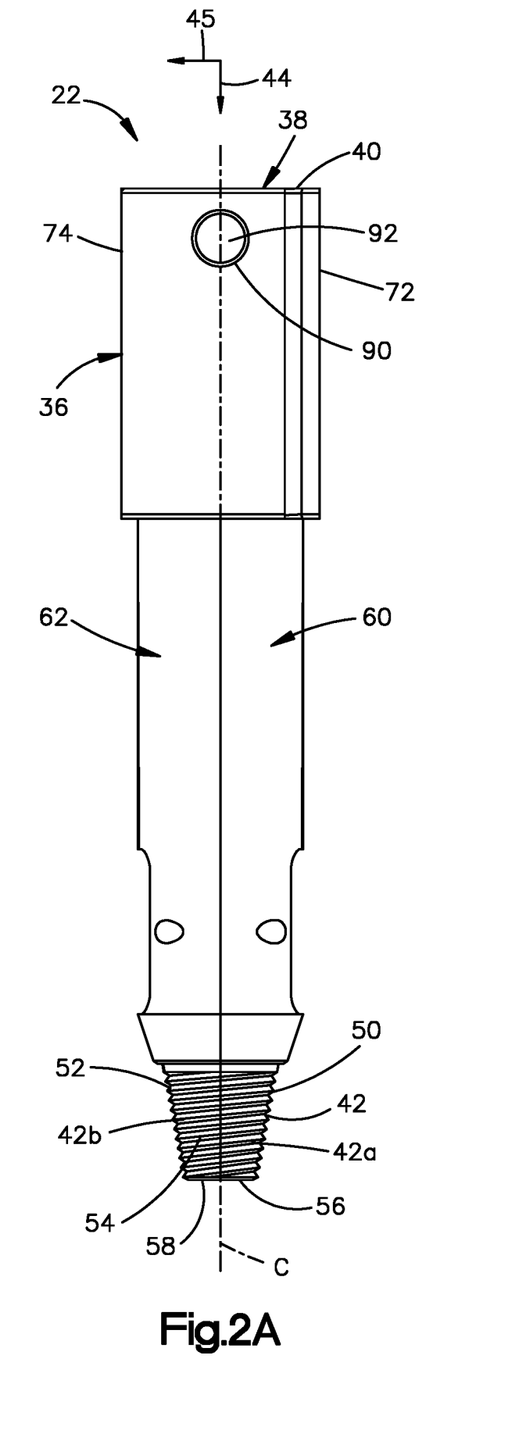
FIG. 2A is a side elevation view of a separable surgical guide instrument constructed in accordance with one embodiment, shown in a closed position.
Figure 2B:
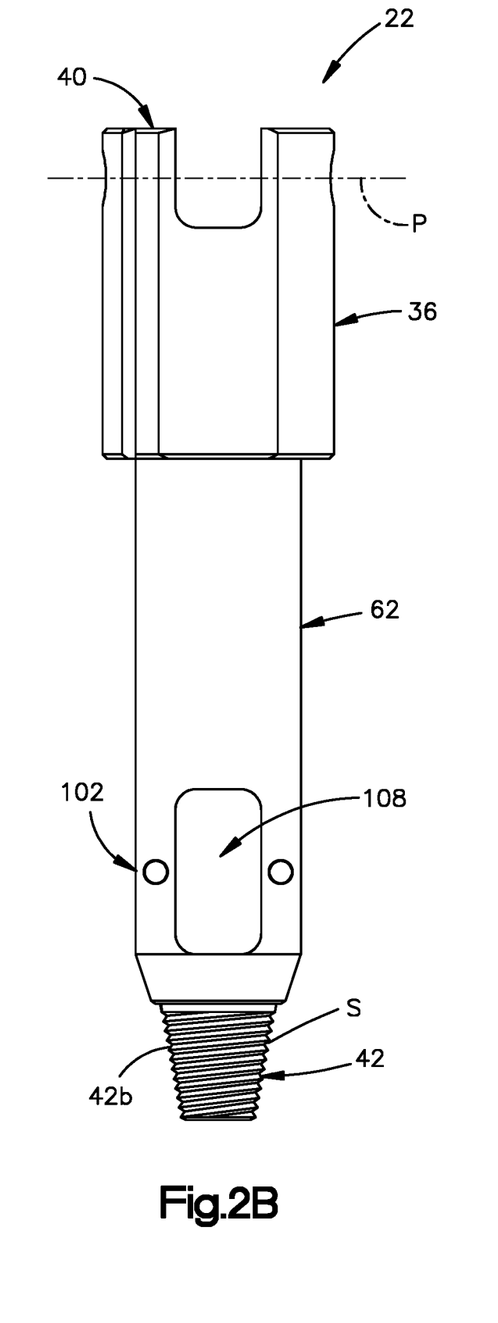
FIG. 2B is another side elevation view of the separable surgical guide instrument illustrated in FIG. 2A.
Figure 2C:
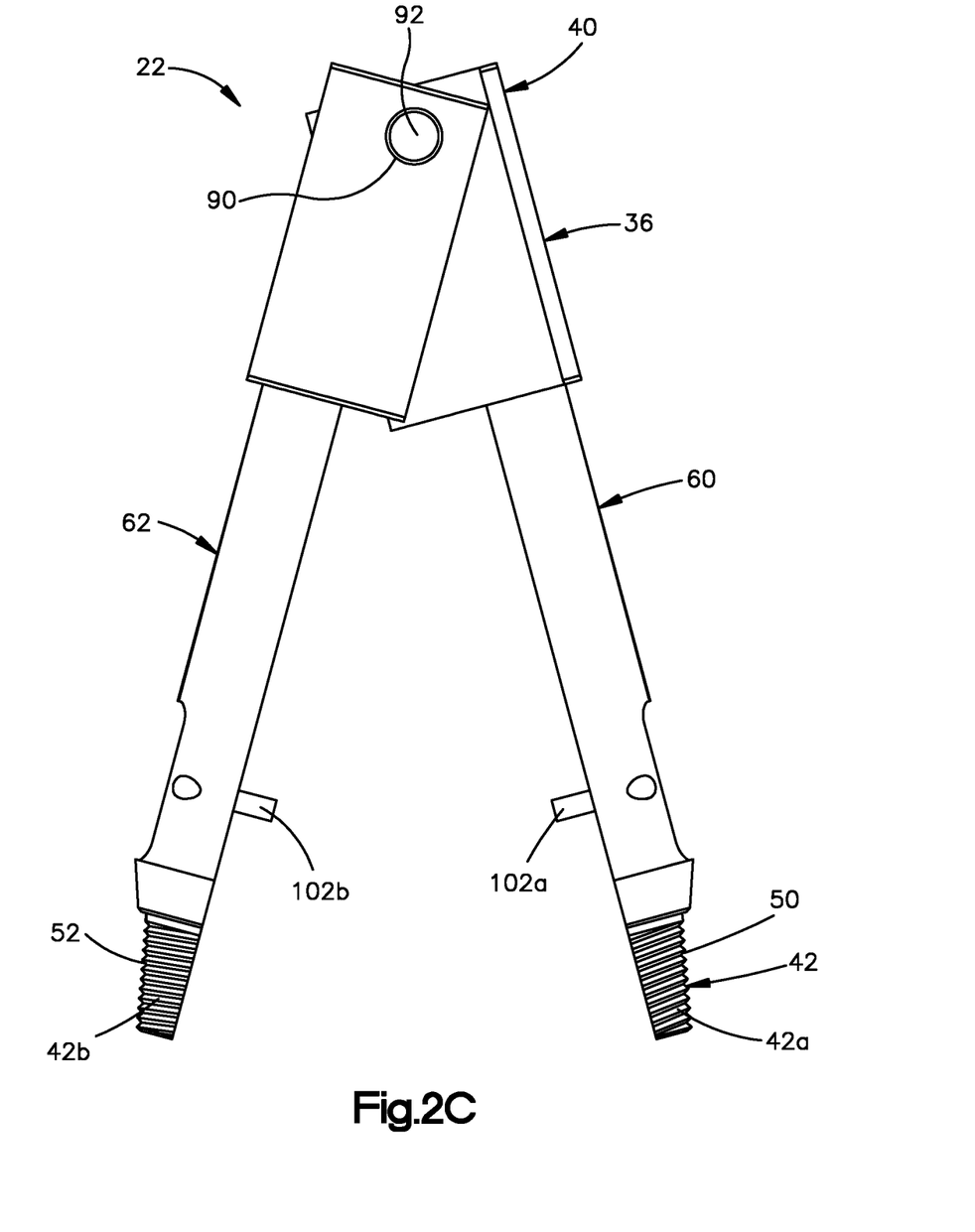
FIG. 2C is a side elevation view of the separable surgical guide instrument illustrated in FIG. 2A, shown in an open position.
Figure 2D:
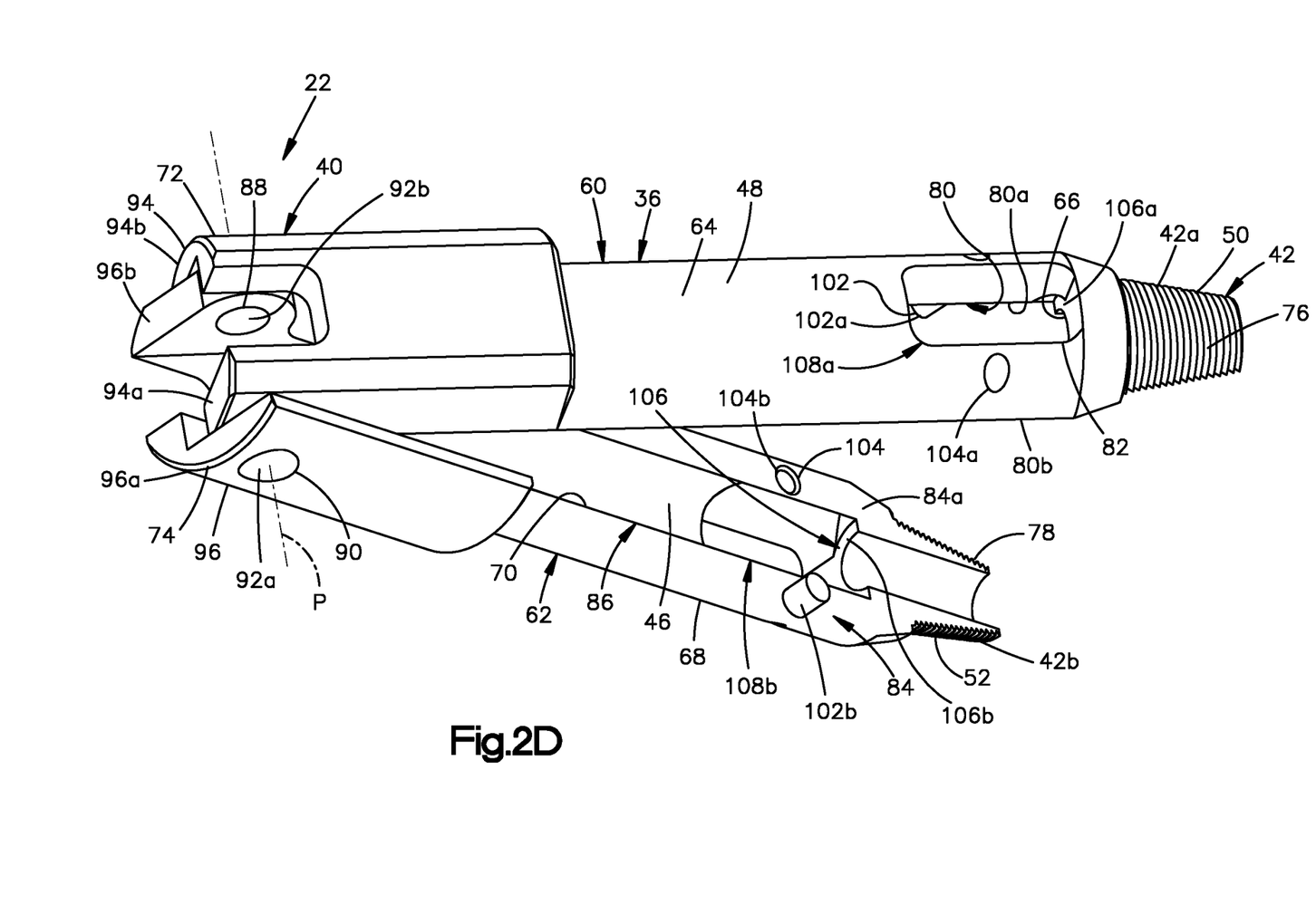
FIG. 2D is a perspective view of the separable surgical guide instrument illustrated in FIG. 2C, shown in the open position.

Referring now to FIG. 2D, as described above, the first and second guide members 60 and 62 can be pivotally coupled to each other. For instance, the first and second guide members 60 and 62 can be directly pivotally attached to each other. Alternatively, the first and second guide members 60 and 62 can be indirectly pivotally attached to each other. For instance, the first and second guide members 60 and 62 can be attached to an intermediate structure such that the first and second guide members 60 and 62 are pivotally coupled to each other. Thus, it can be said that the first and second guide members 60 and 62 are pivotally coupled to each other such that at least one or both of the first and second guide members 60 and 62 is pivotable with respect to the other of the first and second guide members 60 and 62 about the pivot axis P. In accordance with one embodiment, at least one or both of the first and second guide members 60 and 62 is pivotable about the other of the first and second guide members 60 and 62 about the pivot axis P. The separable surgical guide instrument 22 can include a pivot pin 92 that pivotally couples the first guide member 60 to the second guide member 62 at the pivot axis P.

Thus, the pivot pin 92 can define the pivot axis P. At least one of the first and second guide members 60 and 62 is configured to pivot relative to the other of the first and second guide members 60 and 62 about the pivot axis P. In accordance with one embodiment, the first and second guide members 60 and 62 are pivotally coupled to each other about the pivot axis P that is perpendicular to the longitudinal direction 44. For instance, the pivot axis P can intersect the central axis C, and can be oriented perpendicular to the central axis C, for instance when the guide body 36 is in the closed position. The first and second proximal end portions 72 and 74 can be pivotally coupled to each other. For instance, the first and second proximal end portions 72 and 74 can be directly pivotally attached to each other. Alternatively, the first and second proximal end portions 72 and 74 can be indirectly pivotally attached to each other. For instance, the first and second proximal end portions 72 and 74 can be attached to an intermediate structure such that first and second proximal end portions 72 and 74 are pivotally coupled to each other. Thus, it can be said that the first and second proximal end portions 72 and 74 are pivotally coupled to each other such that at least one or both of the first and second proximal end portions 72 and 74 is pivotable with respect to the other of the first and second proximal end portions 72 and 74. In accordance with one embodiment, at least one or both of the first and second proximal end portions 72 and 74 is pivotable about the other of the first and second proximal end portions 72 and 74.

In one example, the first guide member 60 can define a first aperture 88 that extends at least into the first proximal end portion 72. For instance, the first aperture can extend through the first proximal end portion 72. Similarly, the second guide member 62 can define a second aperture 90 that extends at least into the second proximal end portion 74. For instance, the second aperture 90 can extend through the second proximal end portion 74. The pivot pin 92 can extend at least into or through the first and second apertures so as to pivotally couple the first guide member 60 to the second guide member 62. For instance, the first proximal end portion 72 can include at least one arm 94, and the second proximal end portion 74 can include at least one arm 96. The first aperture can extend at least into the at least one arm 94 of the first proximal end portion 72, and the second aperture 90 can extend at least into at least one arm 96 of the second proximal end portion 74.

For instance, the first proximal end portion 72 can define a first arm 94a and a second arm 94b, and the second proximal end portion 74 can define a third arm 96a and a fourth arm 96b. The first arm 94a can be pivotally coupled to the third arm 96a, and the second arm 94b can be pivotally coupled to the fourth arm 96b. For instance, the first aperture can extend at least into or through each of the first and second arms 94a and 94b, and the second aperture can extend at least into or through each of the third and fourth arms 96a and 96b. The separable surgical guide instrument 22 can include first and second pivot pins 92a and 92b, respectively. The first pivot pin 92a can extend at least into or through the first and third arms 94a and 96a so as to pivotally couple the first arm 94a to the third arm 96a. The second pivot pin 92b can extend at least into or through the second and fourth arms 94b and 96b so as to pivotally couple the second arm 94b to the fourth arm 96b. The first and second pivot pins 92a and 92b can be aligned with each other along the pivot axis P, and can define the pivot axis P. The first and second pivot pins 92a and 92b can be spaced from each other along the pivot axis P so as to define a gap therebetween that is aligned with the guide aperture 38. The first arm 94a can be disposed between the central axis C and the third arm 96a, and the fourth arm 96b can be disposed between the central axis C and the second arm 94b. For instance, the first and third arms 94a and 96a can be disposed on a first side of the central axis C, and the second and third arms 94b and 96c can be disposed on a second side of the central axis C that is opposite the first side. The first and second guide members 60 and 62 can be constructed to be identical with respect to each other.

With continuing reference to FIGS. 2A-2D, the first and second guide members 60 and 62 are movable between the open position and the closed position. When the first and second guide members 60 and 62 are in the closed position, the respective first and second distal end portions 42a and 42b can be threadedly inserted into, and threadedly removed from, the threaded bone fixation aperture 30. When the first and second distal end portions 42a and 42b are removed from the bone fixation aperture 30, a force can be applied to at least one or both of the first and second guide members 60 and 62 that urges the at least one or both of the first and second guide members 60 and 62 away from the other of the first and second guide members 60 and 62, thereby causing the first and second guide members 60 and 62 to move from the closed position to the open position. When the first and second guide members 60 and 62 are in the open position, the bone anchor head 26a is movable into the bone fixation aperture 30. Thus, the bone anchor head 26a can be rotated so as to threadedly purchase with the bone plate 24 in the bone fixation aperture 30. The force can be applied to the at least one or both of the first and second guide member 60 and 62 manually or through instrumentation. Alternatively, insertion of the bone anchor 26 in a distal direction from the proximal end 40 to the distal end 42 can apply the force to the first and second guide members 60 and 62 that causes one or both of the first and second guide members 60 and 62 to move away from the other of the first and second guide members 60 and 62. A proximal direction is defined opposite the distal direction, and thus in a direction from the distal end 42 toward the proximal end 40.

For instance, the inner surface 46 can define a shoulder 106 that projects radially inward toward the central axis C. In one example, the first guide member 60 can define a first shoulder portion 106a that projects radially inward toward the central axis C from the first inner surface 66. The second guide member 62 can define a second shoulder portion 106b that projects radially inward toward the central axis C from the second inner surface 70. The first and second shoulder portions 106a and 106b can combine to define the shoulder 106 when the first and second guide members 60 and 62 are in the closed position. Thus, when the first and second guide members 60 and 62 are in the closed position, the bone anchor head 26a can be driven through the guide aperture 38 until the bone anchor head 26a contacts the shoulder 106. Further insertion of the bone anchor 26 through the guide aperture 38 in the distal direction can cause the anchor head 26a to contact the shoulder 106. For instance, the anchor head 26a can contact at least one or both of the first and second shoulder portions 106a-b. Thus, the anchor head 26a can apply a force to one or both of the first and second shoulder portions 106a-b that biases the one or both of the first and second shoulder portions 106a-b away from the other of the first and second shoulder portions 106a-b, which urges at least one of the first and second distal end portions 42a and 42b away from the other of the first and second distal end portions 42a and 42b. Thus, when the bone anchor head 26a or other location of the bone anchor 26 abuts the shoulder 106 and continues to be driven in the distal direction, the bone anchor 26 can cause the first and second anchor members to move from the closed position to the open position. Once the first and second shoulder portions 106a and 106b have been separated from each other such that the gap defined therebetween along a direction perpendicular to the central axis C is greater than the cross-sectional dimension (e.g., diameter) of the bone anchor head 26a, the bone anchor head 26a and the bone anchor shaft 26b can be driven completely through the guide aperture 38 and into the bone fixation aperture 30 of the bone plate 24.

Referring now to FIGS. 2B and 2D, the separable surgical guide instrument 22 defines at least one window 108 that through the guide body 36 from the outer surface 48 to the inner surface 46 so as to provide visibility of the guide aperture 38 from a location external from the separable surgical guide instrument 22. For instance, the window 108 can extend through one or both of the first and second guide members 60 and 62, from the respective inner surface to the respective outer surface. In one example, the instrument 22 includes a first window 108a that extends through the first guide member 60 from the first outer surface 64 to the first inner surface 66. The instrument 22 can further include a second window 108b that extends through the second guide member 62 from the second outer surface 68 to the second inner surface 70. The first and second windows 108a and 108b can be radially opposite each other, such that a straight line that intersects the central axis C can extend through each of the first and second windows 108a and 108b. The first and second windows 108a and 108b can be disposed at a location between the pivot axis P and the distal end 42. For instance, the first and second windows 108a and 108b can be spaced from the shoulder 106 in the proximal direction. Thus, the anchor head 26a can be visible through the first and second windows 108a and 108b before the anchor head 26a abuts the shoulder 106 as the bone anchor 26 travels through the guide aperture 38 in the distal direction.

Figure 3A:
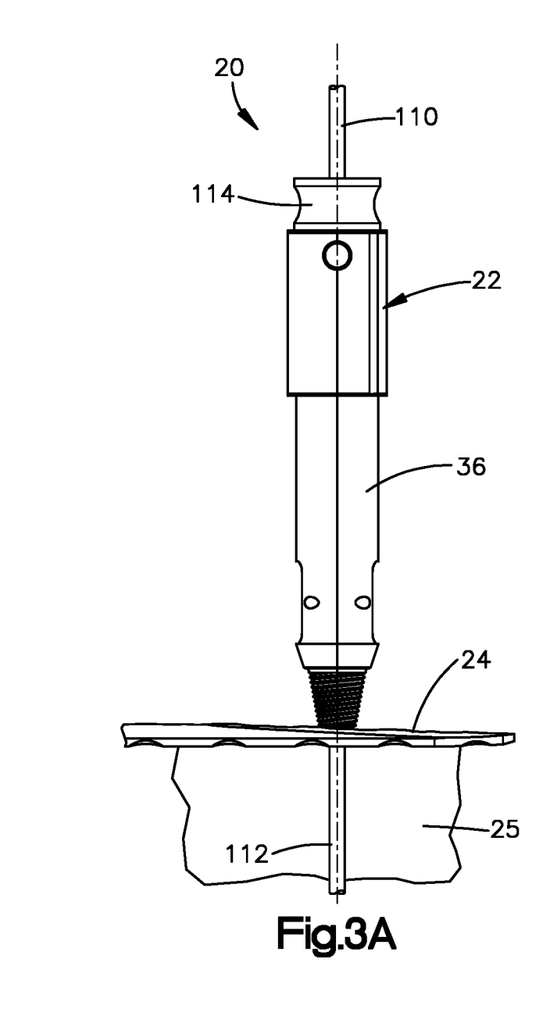
FIG. 3A is a side elevation view of the separable surgical guide instrument illustrated in FIG. 2A, shown coupled to a bone plate, showing a drill bit inserted through a cannula of the separable screw guide instrument and a hole of the bone plate.
Figure 3B:
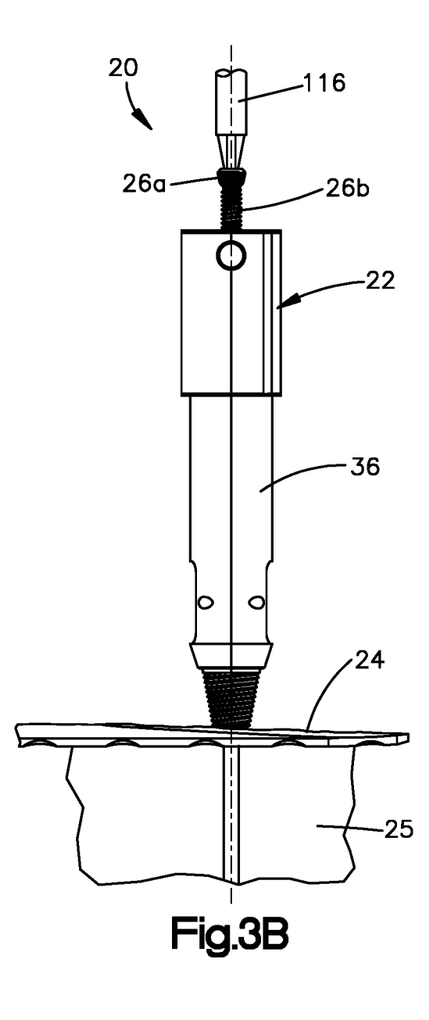
FIG. 3B is a side elevation view of the separable surgical guide instrument illustrated in FIG. 3A, shown coupled to the bone plate, showing insertion of a bone anchor into the cannula of the separable screw guide instrument.
Figure 3C:
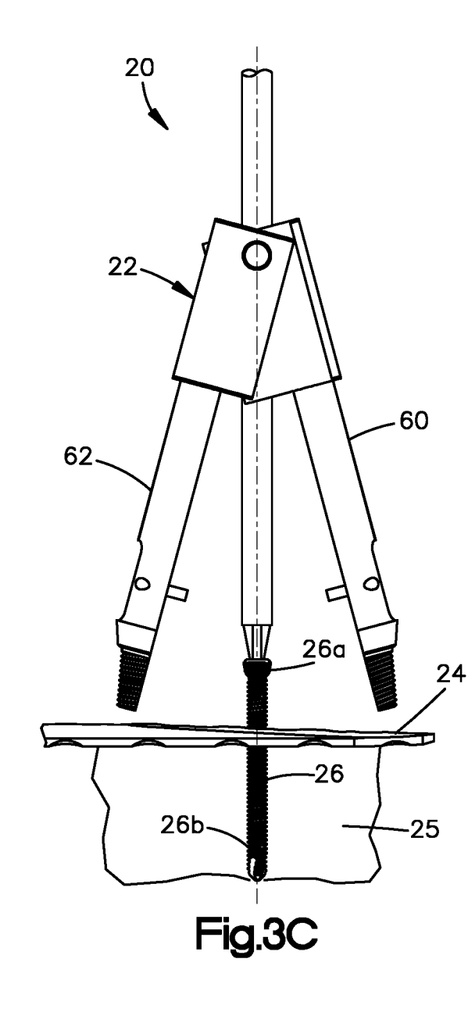
FIG. 3C a side elevation view of the separable surgical guide instrument shown decoupled from the bone plate an in the open position, showing further insertion of the bone anchor toward the bone plate.

Operation of the bone fixation assembly 20 will now be described with further reference to FIGS. 3A-3C. In one example, the bone plate 24 can be positioned adjacent the underlying bone 25. In one example, the bone plate 24 can abut the underlying bone 25. In another example, the bone plate 24 can be spaced from the underlying bone 25. As illustrated in FIG. 3A, the bone fixation assembly 20 can include a surgical drill 110 having a drill bit 112 that is configured to create an opening 109 in the underlying bone 25. The distal end 42 can be inserted into a select one of the bone fixation apertures 30 of the bone plate 24 while the guide body 36 is in the closed position. In this regard, it should be appreciated that the guide body 36 can be inserted minimally invasively through the soft tissue and into the select one of the bone fixation apertures 30. The distal end 42 can be secured in the select one of the bone fixation apertures 30. For instance, the distal end 42 can be rotated with respect to the bone plate 24 along a first direction of rotation about the central axis C so as to cause the distal end 42 to threadedly mate with the bone plate 24 in the select one of the bone fixation apertures 30. For instance, the instrument 22 can be rotated about the central axis C, which causes the distal end 42 to threadedly mate with the bone plate 24 in the select one of the bone fixation apertures 30.

Once the distal end 42 is secured to the bone plate 24 in the bone fixation aperture 30, the central axis C can coincide with a central axis of the bone fixation aperture 30. Next, the surgical drill bit 112 can be inserted through the guide aperture 38 and can create the opening in the underlying bone 25. The opening can be a pilot opening that guides the advancement of the bone anchor 26 into the underlying bone 25. The bone fixation assembly 20 can further include a drill guide 114 that can be supported by the guide body 36. For instance, the drill guide 114 can be supported at the proximal end of the surgical guide instrument 22 when the surgical guide instrument is in the closed position. For instance, the drill guide 114 can extend out from the proximal end of the surgical guide instrument 22. Alternatively or additionally, the drill guide can extend into the guide aperture 38 of the surgical guide instrument 22. The drill guide 114 can define a drill aperture that is sized to receive the drill bit 112 and guide the drill bit 112 through the guide aperture 38 to the underlying bone 25. The drill aperture can be elongate along a central axis that is aligned with the central axis C and the central axis of the bone fixation aperture when the distal end 42 is secured to the bone plate 24 in the bone fixation aperture 30.

Once the drill bit 112 has created the opening in the underlying bone 25, the drill bit 112 can be removed from the separable surgical guide instrument 22. If the bone fixation assembly 20 includes the drill guide 114, the drill bit 112 can be removed from the drill guide 114, and thus also from the separable surgical guide instrument 22. Once the drill bit 112 has been removed, the drill guide 114, if included in the bone fixation assembly 20, can also be removed from the separable surgical guide instrument 22. It should be appreciated that the opening in the underlying bone 25 created by the surgical drill 110 can be elongate along a central axis that is aligned with the central axis C. Accordingly, the bone anchor 26 can be driven into the guide aperture 38 along the distal direction. In this regard, it should be appreciated that the bone fixation assembly 20 can include a driver 116 that is configured to attach to the bone anchor head 26a such that the driver 116 is rotatably coupled to the bone anchor 26. For instance, the driver 116 can be inserted into a socket defined by the bone anchor head 26a. Alternatively, the driver can define a socket that receives the bone anchor head 26a. Because the driver 116 is rotatably coupled to the bone anchor 26 when attached to the bone anchor head 26a, rotation of the driver 116 causes the bone anchor 26 to rotate.

The driver 116 can be advanced into the guide aperture 38 in the distal direction so as to advance the bone anchor 26 through the guide aperture 38 in the distal direction. When the bone anchor head 26a reaches a predetermined location in the guide aperture 38, the distal end 42 can be removed from the bone fixation aperture 30. For instance, visibility of the bone anchor head 26a through the at least one window 108 from a location external to the guide body 36 can be an indicator that the shaft 26b of the bone anchor 26 has entered the bone 25. In one example, visibility of the bone anchor head 26a through the at least one window 108 from a location external to the guide body 36 can be an indicator that the shaft 26b of the bone anchor 26 has entered the opening 109 created by the surgical drill 100. Thus, the distal end 42 of the separable surgical guide instrument 22 can be removed from the bone fixation aperture 30. The location external to the guide body 36 can define a view trajectory to the bone anchor head 26a that is oriented in a direction perpendicular to the central axis C or angularly offset with respect to the central axis C as desired. For instance, the view trajectory can be within an angle within a range between zero and ninety degrees, such as between zero and sixty degrees, for instance between zero and thirty degrees, with respect to the direction that is perpendicular to the central axis C. It should be appreciated that the distal end of the shaft 26b can extend from the bone anchor head 26a a first distance, and the at least one window 108 can be spaced from the distal end 42 a second distance that is less than the first distance. Accordingly, the shaft 26b can be driven into the underlying bone 25 before the anchor head 26a is visible through the at least one window 108 from the location external to the guide body 36.

When the bone anchor head 26a is visible through the at least one window 108 from the location external to the guide body 36, the bone anchor shaft 26b has been driven at least partially into underlying bone 25. For instance, the bone anchor shaft 26b can be driven into the opening created by the surgical drill 110. Alternatively, it should be appreciated that the bone anchor shaft 26b can be driven into the underlying bone 25 without first drilling the opening in the bone 25. The bone anchor shaft 26b can be threaded so as to threadedly purchase with the underlying bone 25 as it is driven into the underlying bone 25.

When the bone anchor shaft 26b has been inserted through the guide aperture 38 a predetermined distance in the distal direction such that at least a portion of the shaft 26b has been driven into the underlying bone 25, the distal end 42 can be removed from the bone fixation aperture 30. For instance, when the bone anchor head 26a is visible through the at least one window 108 from the location external to the guide body 36, the shaft 26b has penetrated the underlying bone 25. Thus, the guide body 36 can be rotated in a second direction of rotation opposite the first direction of rotation with respect to the bone plate 24, thereby threadedly decoupling the distal end 42 from the bone plate 24, and in particular from the threaded inner surface of the bone fixation aperture 30. Once the distal end 42 is removed from the bone fixation aperture 30, the guide body 36 can be moved from the closed position to the open position in the manner described above. In one example, the bone anchor 26 can be advanced in the guide aperture 38 in the distal direction until the anchor head 26a contacts the shoulder 106, which urges the guide body 36 to the open position. As the shaft 26b is further advanced in the underlying bone 25, the head 26a advances toward the bone plate 24 until the anchor head 26a becomes seated in the bone fixation aperture 30. If the bone plate 24 is threaded in the bone fixation aperture 30, and the anchor head 26a is correspondingly threaded, rotation of the bone anchor 26 relative to the bone plate 24 can causes the anchor head 26a to threadedly mate with the bone plate 24 in the bone fixation aperture 30. Alternatively, the anchor head 26a can be unthreaded and seat in the bone fixation aperture 30 so as to apply a compressive force against the bone plate 24 toward the underlying bone.

Figure 4:
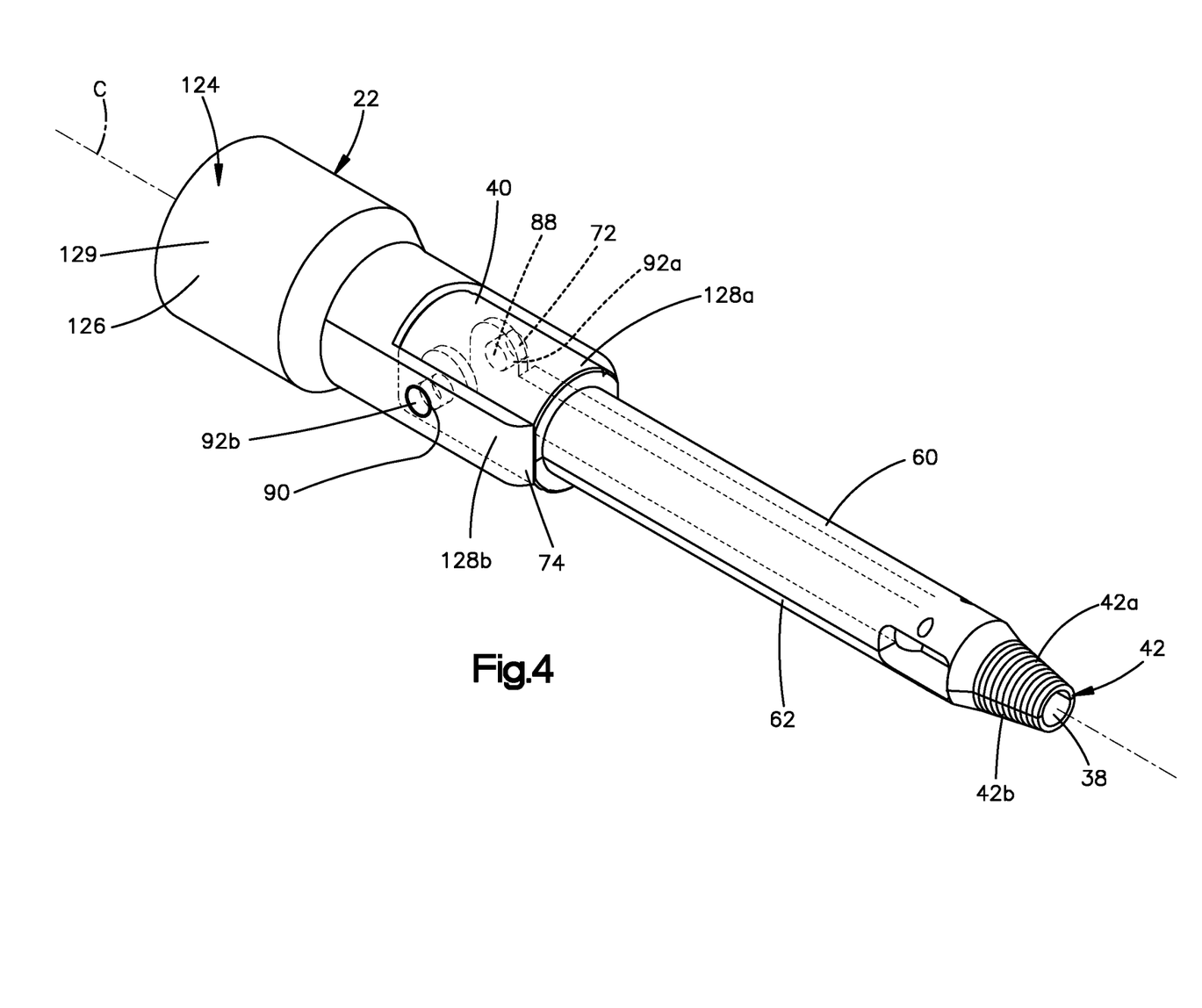
FIG. 4 is a perspective view of a separable surgical guide instrument constructed in accordance with another embodiment.

Referring now to FIG. 4, the separable surgical guide instrument 22 can be constructed as described above with respect to FIGS. 2A-2D unless otherwise indicated. Further, the separable surgical guide instrument 22 can operate as described above with respect to FIGS. 3A-3C. As illustrated in FIG. 4, the separable surgical guide instrument 22 can include a grip member 124 that is attached to the guide body 36. For instance, the grip member 124 can be attached to the proximal end 40 of the guide body 36. The grip member 124 can define a knob 126 and first and second attachment arms 128a and 128b that extend from the knob 126. The knob 126 can define an outer grip surface 129. The outer grip surface 129 can be knurled or define any suitable alternatively constructed texture as desired. Thus, the grip surface 129 can be gripped by a user and rotated about the central axis C. Alternatively, a driving instrument can couple to the instrument 22 so as to rotate the guide body 36 about the central axis C. The first attachment arm 128*a* can be pivotally attached to the first proximal end portion 72 of the first guide member 60. Similarly, the second attachment arm 128*b* can be pivotally attached to the second proximal end portion 74 of the second guide member 62. The grip member 124 can define an aperture that extends through the knob 126 along the longitudinal direction 44 and is aligned with the central axis C. Accordingly, the drill bit 112 can extend through the knob 126 and into the guide aperture 38. Similarly, the bone anchor 26 can extend through the knob 126 and into the guide aperture 38.

For instance, the first aperture 88 can extend through the first proximal end portion 72 and the first attachment arm 128*a*. The second aperture 90 can extend through the second proximal end portion 74 and the second attachment arm 128*b*. The first pivot pin 92*a* can be disposed in the first aperture, and thus can pivotally couple the first attachment arm 128*a* to the first proximal end portion 72. The second pivot pin 92*b* can be disposed in the second aperture 90, and thus can pivotally couple the second attachment arm 128*b* to the second proximal end portion 74. Accordingly, the first proximal end portion 72 can pivot with respect to the first attachment arm 128*a* about the pivot axis defined by the first pivot pin 92*a*. The second proximal end portion 74 can pivot with respect to the second attachment arm 128*b* about the pivot axis also defined by the second pivot pin 92*b*. Thus, the first and second pivot pins 92*a* and 92*b* can be aligned with each other so as to define the pivot axis in the manner described above. The first and second proximal end portions 72 and 74 can pivot about the pivot axis so as to move the first and second guide members 60 and 62 toward and away from each other between the closed position and the open position as described above. For instance, the second guide member 62 can include an extension in the proximal direction that defines a hub 99 that overlaps the proximal end of the first guide member 60, and partially defines one or both of the first and second apertures 88 and 90. The proximal end of the first guide member 60 can also partially define one or both of the first and second apertures 88 and 90. In this regard, it should be appreciated that the first and second guide members 60 and 62 can be constructed asymmetrically with respect to each other.

It should be further appreciated that the grip member 124 can define an intermediate member that indirectly pivotally couples the first guide member 60 with respect to the second guide member 62. The first and second guide members 60 and 62 can pivotally separate from each other about the pivot axis P without causing the grip member 124, and in particular the outer grip surface 129, to separate. Thus, the outer grip surface 129 can be circumferentially continuous both when the separable surgical guide instrument 22 is in the open position and when the separable surgical guide instrument 22 is in the closed position. As a result, the user can grip the outer grip surface 129 both when the separable surgical guide instrument is in the open position and when the separable surgical guide instrument is in the closed position.

The foregoing description is provided for the purpose of explanation and is not to be construed as limiting the electrical connector. While various embodiments have been described with reference to preferred embodiments or preferred methods, it is understood that the words which have been used herein are words of description and illustration, rather than words of limitation. Furthermore, although the embodiments have been described herein with reference to particular structure, methods, and embodiments, the electrical connector is not intended to be limited to the particulars disclosed herein. For instance, it should be appreciated that structure and methods described in association with one embodiment are equally applicable to all other embodiments described herein unless otherwise indicated. Those skilled in the relevant art, having the benefit of the teachings of this specification, may effect numerous modifications to the electrical connector as described herein, and changes may be made without departing from the spirit and scope of the electrical connector, for instance as set forth by the appended claims.

What is claimed is:

1. A method of fixing a bone plate to an underlying bone, the method comprising the steps of:
    placing a bone plate against an underlying bone, wherein the bone plate includes an interior surface that defines a bone fixation aperture, and at least a portion of the interior surface is threaded;
    inserting a threaded distal end of a separable surgical guide instrument into the bone fixation aperture of the bone plate, such that the threaded distal end threadedly mates with the interior surface in the bone fixation aperture;
    inserting a bone screw having a shaft and a threaded head into a guide aperture of the separable surgical guide instrument such that the shaft is driven through the bone fixation aperture and into the underlying bone;
    after the second inserting step, threadedly disengaging the threaded distal end from the interior surface, and removing the distal end from the bone fixation aperture;
    expanding the distal end of the separable surgical guide instrument; and
        driving the threaded head through the guide aperture past the distal end, and threadedly engaging the threaded head with the threaded interior surface in the bone fixation aperture.

2. The method as recited in claim 1, wherein the distal end includes a first distal end portion and a second distal end portion, and the expanding step comprises pivoting at least one of the first and second distal end portions with respect to the other of the first and second distal end portions.

3. The method as recited in claim 2, wherein the pivoting step comprises pivoting each of the first and second distal end portions with respect to the other of the first and second distal end portions.

4. The method as recited in claim 2, wherein the expanding step further comprises expanding the distal end from 1) a closed position whereby the first and second distal end portions are concurrently insertable into the bone fixation aperture of the bone plate, and 2) an open position whereby the first distal end portion is spaced from the second distal end portion a sufficient distance such that the first and second distal end portions are not concurrently insertable into the bone fixation aperture.

5. The method as recited in claim 4, wherein the guide aperture is elongate along a longitudinal direction, and the pivoting step comprises pivoting at least one of the first and second distal end portions with respect to the other of the first and second distal end portions about a pivot axis that is oriented perpendicular to the longitudinal direction.

6. The method as recited in claim 4, wherein the first distal end portion defines at least one first thread segment, and the second distal end portion defines at least one second thread segment, further comprising the step of aligning the first and second thread segments along a common helix when the distal end is in the closed position.

7. The method as recited in claim 6, wherein the expanding step brings the first and second thread segments out of alignment with each other.

8. The method as recited in claim 6, further comprising substantially enclosing the guide aperture when the distal end is in the closed position.

9. The method as recited in claim 6, further comprising the step of inserting a projection of the guide body into an opening of the guide body when the distal end is in the closed position.

10. The method as recited in claim 1, wherein the separable surgical guide instrument comprises a guide body that defines the guide aperture, the guide body further defines a guide window that provides visibility of the guide aperture, and the method further comprises the step of identifying the screw head through the window after the bone screw has begun to purchase into bone.

11. The method as recited in claim 10, wherein the expanding step is performed in response to the identifying step.

12. The method as recited in claim 1, wherein the guide aperture is elongate along a central axis, and the guide body defines a shoulder that extends toward the central axis, and the expanding step further comprises the step of contacting the shoulder with the threaded head so as to urge expand the distal end.

13. The method as recited in claim 1, wherein at least a portion of the outer surface of the guide body at the distal end is tapered toward a central axis of the guide aperture along a direction from the proximal end toward the distal end.

14. The method as recited in claim 1, further comprising the step of threadedly removing the distal end from the bone fixation aperture prior to the expanding step.

* * * * *